(12) United States Patent
Okada

(10) Patent No.: US 9,387,034 B2
(45) Date of Patent: Jul. 12, 2016

(54) HIGH-FREQUENCY KNIFE

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 57 days.

(21) Appl. No.: 14/249,159

(22) Filed: Apr. 9, 2014

(65) Prior Publication Data

US 2014/0288554 A1  Sep. 25, 2014

Related U.S. Application Data

(63) Continuation of application No. PCT/JP2013/078083, filed on Oct. 16, 2013.

(30) Foreign Application Priority Data

Oct. 17, 2012  (JP) .................................. 2012-229756

(51) Int. Cl.
*A61B 18/14* (2006.01)
*A61B 18/00* (2006.01)

(52) U.S. Cl.
CPC ............. *A61B 18/14* (2013.01); *A61B 18/1492* (2013.01); *A61B 2018/00083* (2013.01); *A61B 2018/1412* (2013.01); *A61B 2018/1475* (2013.01); *A61B 2218/002* (2013.01)

(58) Field of Classification Search
CPC ............... A61B 18/14; A61B 18/1492; A61B 2018/1412; A61B 2018/1475; A61B 2018/00083; A61B 2018/144
See application file for complete search history.

(56) References Cited

U.S. PATENT DOCUMENTS 7,371,236 B2 * 5/2008 Okada ............................ 606/45
7,618,416 B2 * 11/2009 Ono et al. ...................... 606/45
(Continued)

FOREIGN PATENT DOCUMENTS

EP      1728462 A2    12/2006
EP      2050409 A1     4/2009
(Continued)

OTHER PUBLICATIONS

Office Action issued in Japanese Patent Application No. 2014-514970 mailed on Jul. 29, 2014 (with translation).
(Continued)

*Primary Examiner* — Michael Peffley
(74) *Attorney, Agent, or Firm* — Oliff PLC

(57) ABSTRACT

A high-frequency knife conduit line and opening hole opening communicate allowing fluid to flow between a rod-shaped electrode outer peripheral surface and the opening hole inner peripheral surface. The guide hole is smaller than the opening and is further toward a radial inner side than the opening outer edge and further toward a radial outer side than the rod-shaped electrode. The fluid is released from the opening to the outside of the sheath over the whole circumference of the rod-shaped electrode on the radial outer side while an electrode portion protrudes toward the sheath distal end portion separating a larger-diameter portion from a supporting member. The fluid is injected to the larger-diameter portion front through the guide hole as the opening hole and the guide hole communicate while the electrode portion is pulled back toward the sheath proximal end portion so that the larger-diameter portion abuts against the supporting member.

6 Claims, 13 Drawing Sheets

(56) References Cited

U.S. PATENT DOCUMENTS

| | | | |
|---|---|---|---|
| 8,016,825 B2 * | 9/2011 | Okada | 606/45 |
| 8,425,510 B2 * | 4/2013 | Yamamoto et al. | 606/46 |
| 8,753,337 B2 * | 6/2014 | Okada | 606/45 |
| 2004/0210284 A1 | 10/2004 | Okada | |
| 2005/0072280 A1 | 4/2005 | Ono et al. | |
| 2014/0207134 A1 * | 7/2014 | Wake | A61B 18/14 606/39 |

FOREIGN PATENT DOCUMENTS

| | | |
|---|---|---|
| JP | A-8-299355 | 11/1995 |
| JP | A-2002-301088 | 10/2002 |
| JP | B2-3655664 | 6/2005 |
| JP | B2-4315725 | 8/2009 |
| JP | A-2012-70793 | 4/2012 |
| JP | A-2012-75657 | 4/2012 |
| JP | A-2012-523863 | 10/2012 |
| WO | WO 2010/118818 A1 | 10/2010 |
| WO | 2012042984 A1 | 4/2012 |
| WO | 2014042039 A1 | 3/2014 |

OTHER PUBLICATIONS

International Search Report issued in International Patent Application No. PCT/JP2013/078083 mailed Nov. 12, 2013 (with translation).

Office Action issued in Japanese Patent Application No. 2014-514970 mailed May 27, 2014 (with partial translation).

May 23, 2016 Extended European Search Report issued in European Application No. 138468145.

* cited by examiner

HIGH-FREQUENCY KNIFE

This application is a continuation claiming priority on the basis of Japanese Patent Application No. 2012-229756 filed in Japan on Oct. 17, 2012 and based on PCT/JP2013/078083 filed on Oct. 16, 2013. The contents of both the Japanese Patent Application and the PCT Application are incorporated herein by reference.

BACKGROUND OF THE INVENTION

1. Field of the Invention

The present invention relates to a high-frequency knife for excising a living body tissue or the like.

2. Description of Related Art

In the related art, the treatment of endoscopically excising living body tissues, such as a mucous membrane, is performed. In order to perform such excision treatment, for example, a high-frequency knife described in Japanese Patent No. 3655664 is known.

In this high-frequency knife, a stopper member is coupled to a distal end of a flexible tube. A knife for an electrode is coupled to a distal end of an operating wire inserted into the flexible tube. The knife for an electrode is constituted by a relatively thin linear wire rod formed from a conductive material. A chip (larger-diameter portion) having a larger external diameter than the external diameter of the knife for an electrode is provided at a distal end of the knife for an electrode. By providing the knife for an electrode with the chip, when the tip of the knife for an electrode is unintentionally brought into contact with a tissue, the tissue can be prevented from being damaged.

The tissue coming into contact with the knife for an electrode can be incised by applying a high-frequency voltage through the operating wire in a state where the operating wire is moved (pushed in) to a distal end side with respect to the flexible tube.

In the high-frequency knife including such a larger-diameter chip, a high-frequency knife disclosed in Japan Patent No. 4315725 is known as a high-frequency knife further including a configuration in which the bleeding during incision is cleansed. In the high-frequency knife, a syringe can be detached from and attached to a cock provided at a proximal end portion of the sheath. A ring-shaped insulated chip (supporting member) is coupled to a distal end of the sheath. The insulated chip is formed with a sliding hole, and a pair of liquid-supplying opening portions are arranged around the sliding hole and communicate with an internal space of the sheath.

A conductive operating wire is inserted through the inside of the sheath so as to be movable in an axial direction. A plate-shaped electrode portion (larger-diameter portion) is coupled to the distal end of the operating wire via the rod-shaped electrode portion.

The high-frequency knife configured in this way performs incision of the tissue by applying a high-frequency voltage in a state where the operating wire is pushed in with respect to the sheath to move the rod-shaped electrode portion to the distal end side and the rod-shaped electrode portion is made to protrude from the distal end of the sheath after being introduced into a body cavity through a channel of an endoscope. When there is bleeding from an incision part in the middle of incision, a physiological salt solution (fluid) is injected into the internal space of the sheath from the syringe attached to the cock in a state where the rod-shaped electrode portion is made to protrude. As a result, the injected physiological salt solution can be injected forward from the liquid-supplying opening portions to cleanse a bleeding portion.

On the other hand, when the high-frequency knife is moved within a patient's body, within the channel of the endoscope, or the like, the operating wire is moved to (pulled back) a proximal end side with respect to the flexible tube, and the rod-shaped electrode portion is moved in a non-exposed state.

SUMMARY OF THE INVENTION

A high-frequency knife of a first aspect of the present invention includes a sheath which is flexible and in which a conduit line is formed, the conduit line supplying a fluid therein; a supporting member which is provided on an inner peripheral surface of a distal end portion of the sheath and has electric insulation; and an electrode portion which has a rod-shaped electrode that is capable of advancing and retracting with respect to the supporting member, and a larger-diameter portion provided at a distal end of the rod-shaped electrode. The supporting member is formed with an opening hole which passes through the supporting member in an axial direction of the sheath, into which the rod-shaped electrode is inserted, and which communicates with the conduit line of the sheath. A guide hole is formed in the larger-diameter portion so as to pass through from a proximal end of the larger-diameter portion to a distal end thereof. The conduit line and an opening of the opening hole on a distal end side communicate with each other so that the fluid is capable of flowing through a gap between an outer peripheral surface of the rod-shaped electrode and an inner peripheral surface of the opening hole. The guide hole is smaller than the opening of the opening hole and is located further toward a radial inner side than an outer edge of the opening and further toward a radial outer side than the rod-shaped electrode. The opening and the guide hole overlap each other in the direction of a longitudinal axis of the rod-shaped electrode irrespective of a rotational position centered on the longitudinal axis of the rod-shaped electrode. The opening hole and the guide hole communicate with each other irrespective of the rotational position in a pull-back state where the electrode portion is pulled back toward a proximal end portion of the sheath so that the rod-shaped electrode is accommodated within the sheath without exposing to the outside. The fluid flows from the opening into a space formed so as to be surrounded by the larger-diameter portion and the opening over a whole circumference of the rod-shaped electrode on the radial outer side, and is then injected to a front of the larger-diameter portion through the guide hole from the space.

According to a second aspect of the present invention, in the high-frequency knife of the first aspect, the opening hole may include a larger-diameter hole portion which is formed on a distal end side of the supporting member; and a smaller-diameter hole portion which is formed on a proximal end side of the larger-diameter hole portion, an internal diameter of the smaller-diameter hole portion is smaller than that of the larger-diameter hole portion. The internal diameter of the larger-diameter hole portion may be smaller than an external diameter of the larger-diameter portion. The larger-diameter portion and an edge of the larger-diameter hole portion may abut against each other in the pull-back state.

According to a third aspect of the present invention, in the high-frequency knife of the second aspect, the larger-diameter portion may have electric insulation.

According to a fourth aspect of the present invention, in the high-frequency knife of the third aspect, the electrode portion may include an auxiliary electrode, which is formed on a proximal end side of the larger-diameter portion so as to extend further in a radial direction than the rod-shaped electrode.

According to a fifth aspect of the present invention, in the high-frequency knife of the fourth aspect, the internal diameter of the larger-diameter hole portion may be larger than the radial dimension of the auxiliary electrode, and at least a portion of the auxiliary electrode may enter the larger-diameter hole portion in the pull-back state.

According to a sixth aspect of the present invention, in the high-frequency knife of the fifth aspect, the guide hole may communicate with a through-hole formed in the auxiliary electrode so as to extend in the axial direction of the sheath.

DETAILED DESCRIPTION OF THE INVENTION

First Embodiment

A first embodiment of a high-frequency knife related to the present invention will be described below referring to FIGS. 1 to 26.

Figure 1:
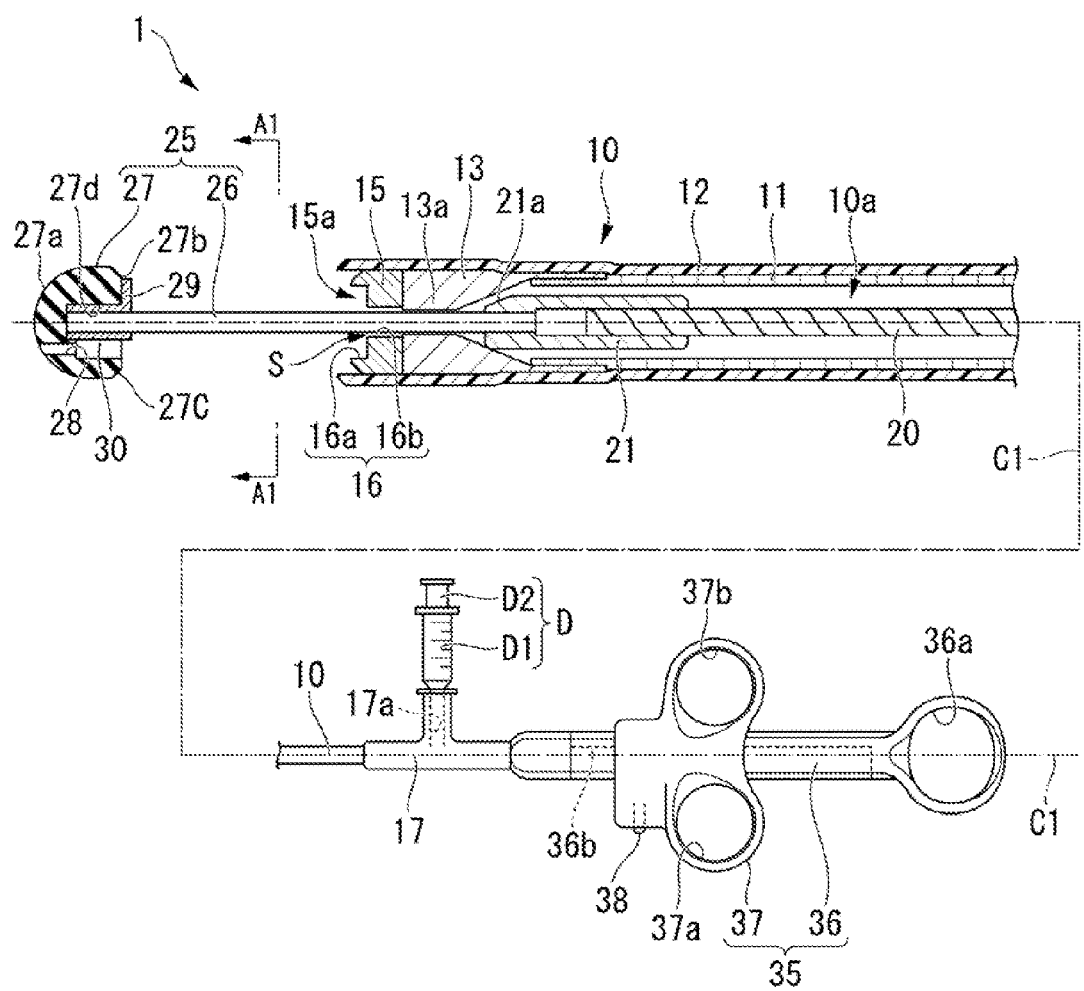
FIG. 1 is a partially cut-away side view when a high-frequency knife of a first embodiment of the present invention is brought into a push-in state.

As shown in FIG. 1, a high-frequency knife 1 of the present embodiment includes a sheath 10, an insulated chip (supporting member) 15 that is provided on an inner peripheral surface of a distal end portion of the sheath 10, an operating wire 20 that is advanceably and retractably inserted into the sheath 10 in the direction of an axis C1 of the sheath 10, and an electrode portion 25 that is provided at a distal end portion of the operating wire 20.

The sheath 10 has an external diameter and flexibility such that the sheath is insertable through a channel (not shown) of an endoscope, and has electrical insulation. The sheath 10 has a closely wound coil 11, an insulating tube 12 that covers an outer peripheral surface of the closely wound coil 11, and a stopper member 13 that is fixed to an inner peripheral surface of a distal end portion of the closely wound coil 11.

The closely wound coil 11 is constituted, for example, by winding a plate-shaped coil without gaps in the direction of the axis C1. The closely wound coil 11 has flexibility such that its shape can be easily changed in accordance with shape changes in an insertion section of the endoscope in a state where the sheath 10 is inserted into the channel of the endoscope.

The insulating tube 12 is formed from, for example, a resin material having heat resistance and flexibility, such as a tetrafluoroethylene material. The insulating tube 12 has an external diameter such that the insulating tube is insertable through the channel of the endoscope.

The stopper member 13 is formed in a tubular shape from a material having insulation. A distal end portion of the stopper member 13 is formed with a thick portion 13a that is made thicker radially inward of the sheath 10 than a proximal end portion of the stopper member 13.

An inner peripheral surface and an outer peripheral surface of a coupling portion between the closely wound coil 11 and the stopper member 13 are formed so as to be almost flush with each other.

The aforementioned insulated chip 15 is fixed to the inner peripheral surface of the insulating tube 12 located further toward the distal end side than the thick portion 13a. The insulated chip 15 is fixed to the insulating tube 12 and the stopper member 13 so that a distal end of the insulating tube 12 is disposed so as to extend further toward the distal end side than the insulated chip 15. The insulated chip 15 is formed in a substantially columnar shape, and is formed with an opening hole 16 that passes through the insulated chip 15 in the direction of the axis C1 and that communicates with an opening 15a formed in a distal end surface of the insulated chip 15, and a conduit line 10a of the sheath 10, respectively.

The opening hole 16 has a larger-diameter hole portion 16a that is formed on the distal end side in the insulated chip 15, and reaches the distal end surface of the insulated chip 15, and a smaller-diameter hole portion 16b that communicates with the larger-diameter hole portion 16a on a proximal end side of the larger-diameter hole portion 16a and is formed to have a smaller internal diameter than the larger-diameter hole portion 16a. In this example, the larger-diameter hole portion 16a and the smaller-diameter hole portion 16b are formed on the axis C1, respectively. The smaller-diameter hole portion 16b reaches a proximal end surface of the insulated chip 15.

It is preferable that the insulated chip 15 be formed from a material having heat resistance and electrical insulation, such as a ceramic material. An inner peripheral surface of the smaller-diameter hole portion 16b is formed so as to be substantially flush with an inner peripheral surface of the thick portion 13a.

A liquid-supply mouthpiece 17 in which an injection port 17a communicating with the conduit line 10a is formed is attached to a proximal end portion of the sheath 10. A syringe (liquid-supply means) D is attachable to and detachable from the injection port 17a. A physiological salt solution (fluid) that is not shown is stored in a syringe body D1 of the syringe D. The physiological salt solution can be supplied to the conduit line 10a through the injection port 17a by pushing the plunger D2 into the syringe body D1 in a state where the syringe body D1 is attached to the injection port 17a.

Metal having conductivity can be suitably used for the operating wire 20.

The electrode portion 25 extends in the direction of the axis C1, and has a rod-shaped electrode 26 having a proximal end portion electrically connected to the distal end portion of the operating wire 20, and a larger-diameter portion 27 provided at a distal end portion of the rod-shaped electrode 26.

The rod-shaped electrode 26 is formed from metal, such as stainless steel having biocompatibility and conductivity. The rod-shaped electrode 26 is advanceably and retractably inserted through the opening hole 16 and the stopper member 13, and the external diameter of the rod-shaped electrode 26 is set so that a gap S is formed between the inner peripheral surface of the smaller-diameter hole portion 16b and the stopper member 13, and an outer peripheral surface of the rod-shaped electrode 26. A stopper-receiving portion 21 formed in a tubular shape from a material having conductivity is attached to an outer peripheral surface of a connecting portion between the rod-shaped electrode 26 and the operating wire 20. The external diameter of the stopper-receiving portion 21 is set to be larger than the internal diameter of the smaller-diameter hole portion 16b.

As will be described below, an inclination portion 21a is formed on an outer peripheral surface of a distal end portion of the stopper-receiving portion 21 so that the conduit line 10a is not sealed at an intermediate portion in the direction of the axis C1 when the stopper-receiving portion 21 is made to abut against the stopper member 13.

The larger-diameter portion 27 is formed in a substantially columnar shape.

The larger-diameter portion 27 has a distal end surface 27a that is formed in the shape of a curved surface that becomes convex toward the distal end side, and a proximal end surface 27b that is flatly formed so as to be orthogonal to the direction of the axis C1. The edge of the proximal end surface 27b is formed with a chamfered portion 27c chamfered so as to have an enlarged diameter towards the distal end side.

Figure 2:
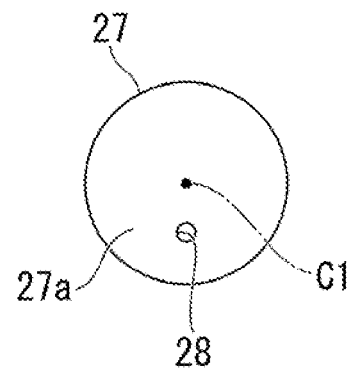
FIG. 2 is a front view of the larger-diameter portion of the high-frequency knife.

An attachment hole 27d extending in the direction of the axis C1 is formed at the center of the proximal end surface 27b of the larger-diameter portion 27. Additionally, the larger-diameter portion 27, as shown in FIGS. 1 and 2, is formed with one guide hole 28 that extends in the direction of the axis C1 and passes through the larger-diameter portion 27. The guide hole 28 is formed so as to have a larger internal diameter on the proximal end side than on the distal end side.

The external diameter of the larger-diameter portion 27 is made larger than the external diameter of the rod-shaped electrode 26, and is made approximately equal to the internal diameter of the sheath 10.

The larger-diameter portion 27 is formed from the same material as the stopper member 13 having electrical insulation.

Figure 3:
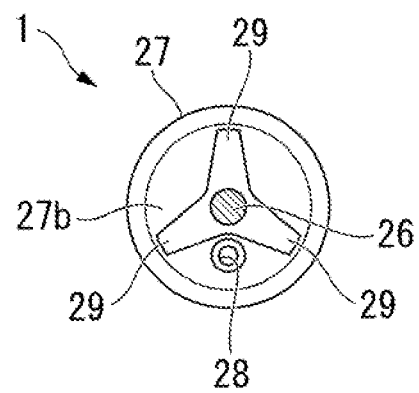
FIG. 3 is a cross-sectional view of cutting line A1-A1 in FIG. 1.

In this example, as shown in FIGS. 1 and 3, three auxiliary electrodes 29 formed in the shape of a square bar that extends in a radial direction of the sheath 10 are provided on the proximal end surface 27b of the larger-diameter portion 27. The three auxiliary electrodes 29 are radially arranged at approximately equal intervals in the circumferential direction of the sheath 10, in FIG. 3 as seen in the direction of the axis C1. The respective auxiliary electrodes 29 are arranged so as to protrude to the proximal end side from the proximal end surface 27b of the larger-diameter portion 27. Additionally, on the proximal end surface 27b, the length from the axis C1 to the distal ends of the respective auxiliary electrodes 29 that extend in the radial direction is set so as to be larger than the radius of the larger-diameter hole portion 16a.

As seen in the direction of the axis C1, the guide hole 28 is provided between a pair of the auxiliary electrodes 29 adjacent to each other in the circumferential direction. That is, the respective auxiliary electrodes 29 are arranged so as not to overlap the guide hole 28.

In this example, as shown in FIGS. 1 and 3, three auxiliary electrodes 29 formed in the shape of a square bar that extends in a radial direction of the sheath 10 are provided on the proximal end surface 27b of the larger-diameter portion 27. The three auxiliary electrodes 29 are radially arranged at approximately equal intervals in the circumferential direction of the sheath 10, in FIG. 3 as seen in the direction of the axis C1. Moreover, the respective auxiliary electrodes 29 are arranged so as not to overlap the guide hole 28. As a result, the respective auxiliary electrodes 29 are arranged so as to protrude to the proximal end side from the proximal end surface 27b of the larger-diameter portion 27. Additionally, on the proximal end surface 27b, the length from the axis C1 to the distal ends of the respective auxiliary electrodes 29 that extend in the radial direction is set so as to be larger than the radius of the larger-diameter hole portion 16a.

The respective auxiliary electrodes 29 are formed from conductive metal, such as stainless steel, integrally with tubular metal fitting 30. The tubular metal fitting 30 is disposed within the attachment hole 27d, and the distal end portion of the rod-shaped electrode 26 is inserted through the tubular metal fitting 30. The tubular metal fitting 30 and the tubular rod-shaped electrode 26 are connected together by welding, are buried within the attachment hole 27d, and are fixed to the larger-diameter portion 27. As a result, the respective auxiliary electrodes 29 are electrically connected to the rod-shaped electrode 26.

The high-frequency knife 1 of the present embodiment, as shown in FIG. 1, includes an operating section 35 provided on the proximal end side of the liquid-supply mouthpiece 17.

The operating section 35 includes an operating section body 36 that is fixed to a proximal end portion of the liquid-supply mouthpiece 17, and an operating slider 37 that is slidable with respect to the operating section body 36. A grooved guide shaft portion 36b is formed along the axis C1 at the operating section body 36. The operating slider 37 is slidable along the axis C1. The operating section body 36 has a finger-hooking ring 36a at a proximal end portion thereof.

The operating slider 37 includes finger-hooking rings 37a and 37b side by side in a direction orthogonal to the axis C1. For this reason, the operating slider 37 can be made to slide in the direction of the axis C1 with respect to the operating section body 36, for example, by putting a surgeon's thumb into the ring 36a of the operating section body 36, putting a surgeon's index finger and middle finger into the rings 37a and 37b of the operating slider 37, and operating the rings with the surgeon's thumb, index finger, and middle finger.

A proximal end side of the aforementioned operating wire 20 is inserted through the liquid-supply mouthpiece 17 and the operating section body 36, and a proximal end portion of the operating wire 20 is fixed to the operating slider 37. Sealant (not shown) for water-tightly sealing the conduit line and the operating wire 20 between the liquid-supply mouthpiece 17 and the operating section body 36 is provided within the liquid-supply mouthpiece 17.

The operating slider 37 includes a connecting connector 38 to which a cord that leads to a high-frequency generator (not shown) is electrically connected.

The connecting connector 38 is electrically connected to the proximal end side of the operating wire 20.

In the high-frequency knife 1 configured in this way, as shown in FIG. 1, the operating wire 20 is pushed into the distal end side with respect to the sheath 10 by moving the operating slider 37 to the distal end side with respect to the operating section body 36; as a result, the stopper-receiving portion 21 abuts against the stopper member 13, and there is positioning in a push-in state where the operating wire 20 is pushed into the distal end side. In this push-in state, the larger-diameter portion 27 and the respective auxiliary electrodes 29 are separated to the distal end side with respect to the insulated chip 15, and the rod-shaped electrode 26 and the respective auxiliary electrodes 29 are exposed to the outside.

Figure 4:
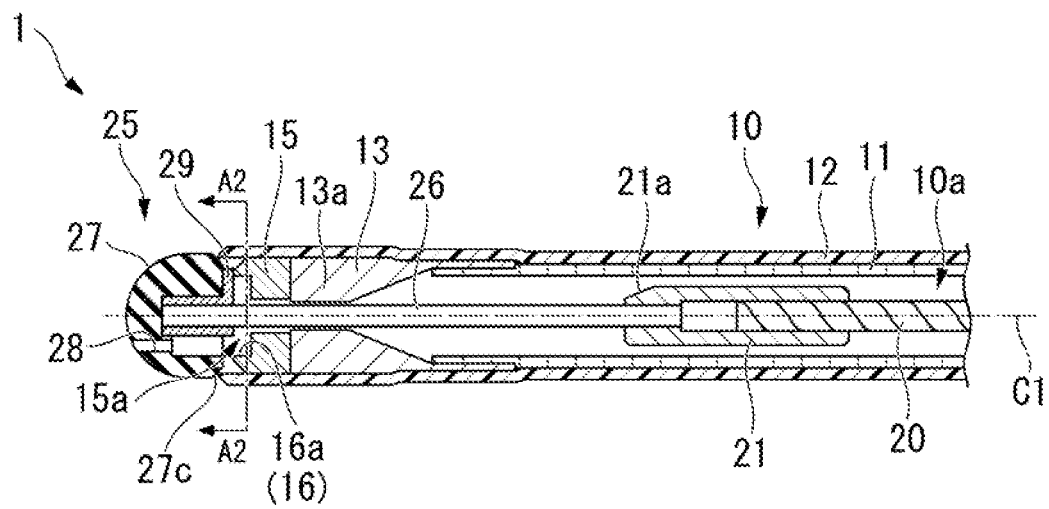
FIG. 4 is a cross-sectional view of a side surface on a distal end side when the high-frequency knife is brought into a pull-back state.
Figure 5:
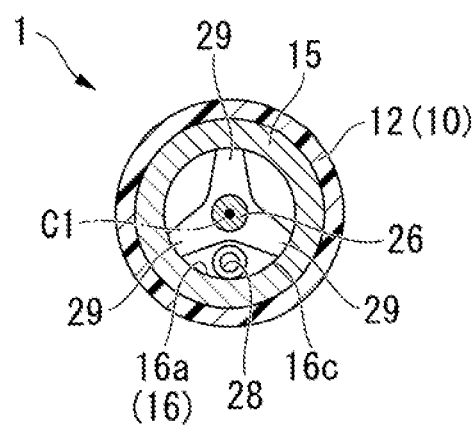
FIG. 5 is a cross-sectional view of cutting line A2-A2 in FIG. 4.

On the other hand, if the operating wire 20 is pulled back to the proximal end side with respect to the sheath 10 by moving the operating slider 37 to the proximal end side with respect to the operation section body 36, as shown in FIGS. 4 and 5, the larger-diameter portion 27 abuts against the insulated chip 15 via the respective auxiliary electrodes 29, whereby there is positioning in a pull-back state where the operating wire 20 is pulled back to the proximal end side.

In this pull-back state, the high-frequency knife 1 is configured as follows. That is, the distal end portion of the sheath 10 covers a portion of the chamfered portion 27c of the larger-diameter portion 27, and the rod-shaped electrode 26 and the respective auxiliary electrodes 29 are brought into a state where these electrodes are accommodated within the sheath 10 and are not exposed to the outside. As the opening hole 16 and the guide hole 28 communicate with each other, a portion of the opening 15a of the opening hole 16 is brought into a non-blocked state. Additionally, as seen in the direction of the axis C1 as shown in FIG. 5, the guide hole 28 is arranged inside an outer edge 16c of the larger-diameter hole portion 16a. As a result, the opening 15a and the guide hole 28 are located in an overlapping manner irrespective of the rotated position of the rod-shaped electrode 26 around the axis C1.

Next, the operation of the high-frequency knife 1 configured as described above will be described. In the following, for example, the operation when excision of a mucous membrane within a body cavity is endoscopically performed using the high-frequency knife 1 will be described. Generally, an observation unit has an opening on the distal end side of the channel that allows a treatment tool, such as the high-frequency knife 1, to be inserted therethrough, an imaging element for acquiring an image of an object to be observed, and the like, and is provided at a distal end portion of the insertion section of the endoscope.

First, although not shown, an injection needle is endoscopically introduced into the body cavity through the channel of the endoscope. At this time, the injection needle is introduced while observing an image, which is acquired by the observation unit of the endoscope, with a display unit, such as a monitor.

Figure 6:
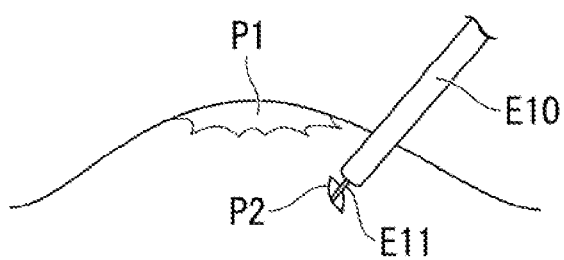
FIG. 6 is a view illustrating a procedure using the high-frequency knife and showing a state where a hole is made in a portion of a mucous membrane.

Using the injection needle, as shown in FIG. 6, a physiological salt solution is injected into a submucosal layer of a lesioned mucous membrane portion P1 that is a target part of the body cavity to be excised, and the lesioned mucous membrane portion P1 is caused to bulge.

Next, a counter-electrode plate (not shown) is worn by a patient. Thereafter, a high-frequency knife E10 having a related-art needlelike electrode (knife unit) E11 is endoscopically introduced similarly. The initial incision of applying an electric current to the electrode E11 to make a hole P2 in a portion of the mucous membrane around the lesioned mucous membrane portion P1 is performed. Then, the high-frequency knife E10 is pulled out and removed from the channel of the endoscope.

Figure 7:
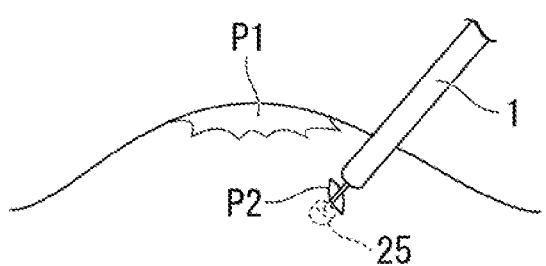
FIG. 7 is a view illustrating the procedure using the high-frequency knife and showing a state where an electrode portion is inserted into the hole of the mucous membrane.

Subsequently, the high-frequency knife 1 of the present embodiment brought into the pull-back state is introduced into the body cavity via an empty channel of the endoscope. The distal end portion of the high-frequency knife 1 is made to protrude from the distal end of the insertion section of the endoscope. Then, the surgeon or an assistant puts his/her fingers into the rings 36a, 37a, and 37b, respectively, pushes the operating slider 37 into the distal end side with respect to the operating section body 36, and brings the high-frequency knife 1 into the push-in state. As shown in FIG. 7, the electrode portion 25 of the high-frequency knife 1 is inserted from the distal end side into the hole P2 that is initially incised.

Figure 8:
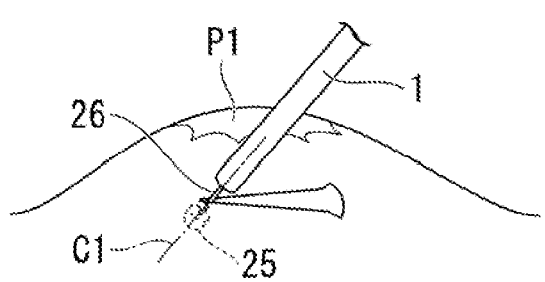
FIG. 8 is a view illustrating the procedure using the high-frequency knife and showing a state where an electrode portion is moved in a transverse direction to perform incision.

Next, the high-frequency generator (not shown) is connected to the connecting connector 38 of the operating section 35. While a high-frequency voltage is applied to the rod-shaped electrode 26 and the auxiliary electrodes 29 via the connecting connector 38 and the operating wire 20 by the high-frequency generator, as shown in FIG. 8, the electrode portion 25 of the high-frequency knife 1 is moved along a predetermined excision direction. For example, if the electrode portion 25 is moved in a transverse direction orthogonal to the axis C1, the mucous membrane coming into contact with the rod-shaped electrode 26 is incised by the rod-shaped electrode 26.

Figure 9:
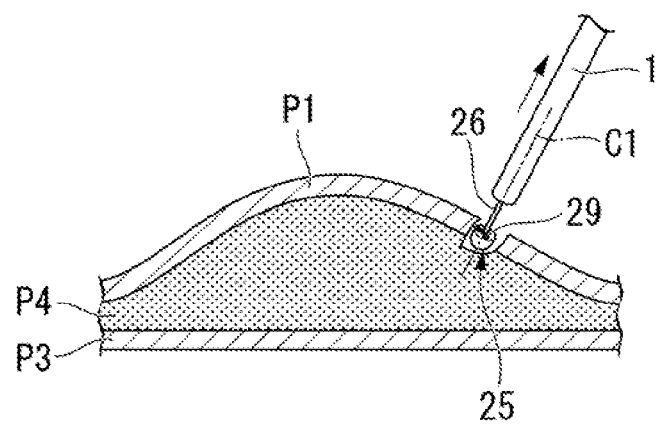
FIG. 9 is a view illustrating the procedure using the high-frequency knife and showing a state where an electrode portion is moved in a longitudinal direction to perform incision.
Figure 10:
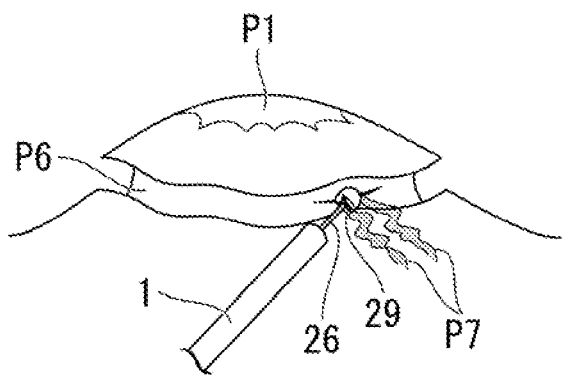
FIG. 10 is a view illustrating the procedure using the high-frequency knife and showing a state where blood has flowed out of an opening of a tissue.

When it is difficult to move the electrode portion 25 in the transverse direction, as shown in FIG. 9, the electrode portion 25 is moved in the longitudinal direction that is the direction of the axis C1. Then, the mucous membrane hooked by the auxiliary electrodes 29 is incised by coming into contact with the auxiliary electrodes 29.

The electrode portion 25 of the high-frequency knife 1 is moved by combining this movement in the longitudinal direction and the aforementioned movement in the transverse direction. Then, the periphery of the lesioned mucous membrane portion P1 is incised in the circumferential direction of the lesioned mucous membrane portion P1.

In the present embodiment, the larger-diameter portion 27 is formed from a material having insulation. For this reason, even if the distal end surface 27a of the larger-diameter portion 27 comes into contact with a non-excised tissue P3, such as a muscle layer, by the movement of the larger-diameter portion 27 in the longitudinal direction, the high-frequency voltage applied to the rod-shaped electrode 26 or the respective auxiliary electrodes 29 does not act on the non-excised tissue P3. Accordingly, the surgeon does not need to perform the complicated operation of moving the rod-shaped electrode 26 at a constant depth so that the non-excised tissue P3 located at a deep portion of a part to be excised, and the rod-shaped electrode 26 do not come into contact with each other.

Symbol P4 in FIG. 9 represents the submucosal layer between the lesioned mucous membrane portion P1 and the non-excised tissue P3.

When the lesioned mucous membrane portion P1 is completely incised in the circumferential direction as described above, as shown in FIG. 10, the rod-shaped electrode 26 and the respective auxiliary electrodes 29 are made to abut against an opening P6 obtained by incising the periphery of the lesioned mucous membrane portion P1, the lesioned mucous membrane portion P1 is sequentially incised combining the movements of the high-frequency knife 1 in the transverse direction and the longitudinal direction, and the lesioned mucous membrane portion P1 is peeled off.

When the lesioned mucous membrane portion P1 is incised, blood P7 may flow out.

Figure 11:
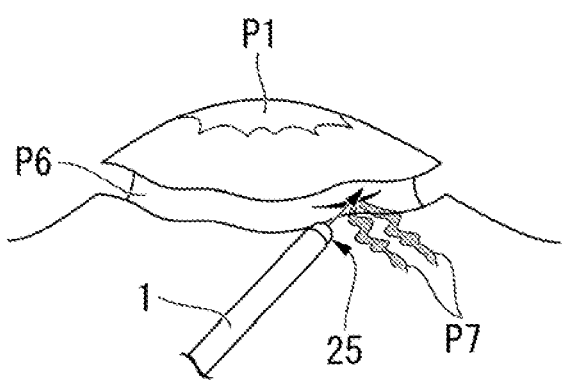
FIG. 11 is a view illustrating the procedure using the high-frequency knife and showing a state where the blood that has flowed out is washed out.

At this time, as shown in FIG. 11, the high-frequency knife 1 is brought into the pull-back state, and the syringe body D1 is attached to the injection port 17a of the liquid-supply mouthpiece 17. If the plunger D2 is pushed in, the physiological salt solution stored in the syringe body D1 is injected to the front of the larger-diameter portion 27 through the liquid-supply mouthpiece 17, the conduit line 10a, the opening hole 16, and the guide hole 28. This cleanses the blood P7. A part out of which the blood P7 has flowed becomes clear, and it is easy to perform treatment of hemostasis.

In the pull-back state, the distal end portion of the sheath 10 covers a portion of the chamfered portion 27c of the larger-diameter portion 27. Therefore, the physiological salt solution does not easily flow in the radial direction out of the portions where the respective auxiliary electrodes 29 abut against the insulated chip 15, and is allowed to flow reliably from the guide hole 28. The treatment of the hemostasis is performed, for example, by inserting a treatment tool for coagulation (not shown) from the channel of the endoscope to coagulate the tissue of a bleeding portion.

By bringing the high-frequency knife 1 into the pull-back state and injecting the physiological salt solution, the distance from the observation unit provided at the distal end portion of the insertion section to a distal end portion of the guide hole 28 of the electrode portion 25 where the physiological salt solution is injected becomes short.

Figure 12:
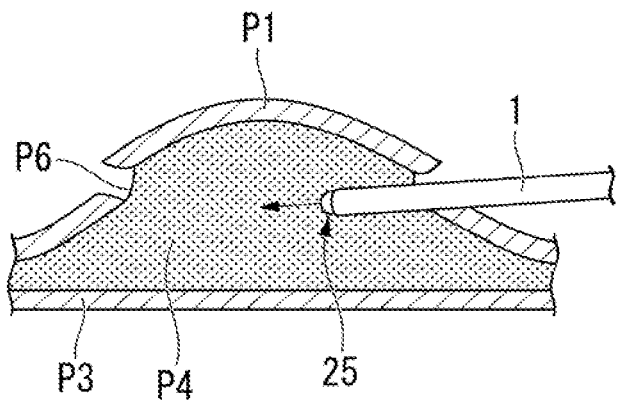
FIG. 12 is a view illustrating the procedure using the high-frequency knife and showing a state where a physiological salt solution is added and injected into a submucosal layer.

Additionally, if time passes since the injection of the physiological salt solution by the aforementioned injection needle, the physiological salt solution injected into the submucosal layer P4 of the lesioned mucous membrane portion P1 may move to a peripheral portion, and the height by which the lesioned mucous membrane portion P1 bulges may become low. At this time, as shown in FIG. 12, the electrode portion 25 of the high-frequency knife 1 brought into the pull-back state is introduced into the submucosal layer P4 through the opening P6. The lesioned mucous membrane portion P1 is caused to bulge again by pushing in the plunger D2 and additionally and locally injecting the physiological salt solution into the submucosal layer P4.

Even at this time, since the physiological salt solution is injected to the front of the larger-diameter portion 27 through the guide hole 28 of the larger-diameter portion 27, the additional and local injection can be easily performed to a desired part of the submucosal layer P4.

Then, the high-frequency knife 1 is returned to the push-in state, and the lesioned mucous membrane portion P1 is completely excised and peeled off. The high-frequency knife 1 is brought into the push-back state, and is pulled out from the inside of the channel of the endoscope to the hand side. Grip forceps (not shown) or the like are inserted through an empty channel of the endoscope. The grip forceps are operated to take out the lesioned mucous membrane portion P1 endoscopically, and a series of treatment is ended.

In the related art, when the bulging height of a lesioned mucous membrane portion becomes low while incision is performed by a high-frequency knife, it is necessary to perform a treatment in the following process. That is, first, the high-frequency knife is pulled out from a channel of an endoscope. Then, an injection needle is inserted into the channel, a physiological salt solution is additionally and locally injected into a submucosal layer of the lesioned mucous membrane portion using this injection needle, and the bulging height of the lesioned mucous membrane portion is adjusted. This injection needle is pulled out from the channel, a high-frequency knife is again inserted into a channel, and the treatment is resumed.

In contrast, in the high-frequency knife 1 of the present embodiment, it is not necessary to pull out the high-frequency knife 1 from the inside of the channel in order to adjust the bulging height of the lesioned mucous membrane portion P1. Thus, a procedure can be performed in a short time.

As described above, according to the high-frequency knife 1 of the present embodiment, a high-frequency current is applied to the rod-shaped electrode 26 via the operating wire 20 in a state where the operating wire 20 is pushed into the distal end side with respect to the sheath 10 to bring the high-frequency knife 1 into the push-in state and the rod-shaped electrode 26 is exposed. A tissue can be incised by bringing the tissue into contact with the rod-shaped electrode 26.

When the larger-diameter portion 27 is made to abut against the insulated chip 15 by pulling the operating wire 20 back to the proximal end side with respect to the sheath 10 and bringing the high-frequency knife 1 into the pull-back state, at least a portion of the opening 15a of the opening hole 16 is brought into the non-blocked state. Here, if the physiological salt solution is supplied to the conduit line 10a of the sheath 10 by the syringe D, the supplied physiological salt solution is injected toward the front of the insulated chip 15 and the larger-diameter portion 27 through the opening hole 16.

Accordingly, when the high-frequency knife is brought into the pull-back state and the rod-shaped electrode 26 is brought into a non-exposed state, the larger-diameter portion 27 does not become an obstacle to injection of the physiological salt solution.

Since it is not necessary to pull out the high-frequency knife 1 from the inside of the channel when the lesioned mucous membrane portion P1 is adjusted to the bulging height, the additional and local injection can be rapidly performed.

As the opening hole 16 of the insulated chip 15 and the guide hole 28 of the larger-diameter portion 27 communicate with each other in the pull-back state, the physiological salt solution can be injected toward the front of the larger-diameter portion 27 through the guide hole 28 communicating with the opening hole 16 even in a state where the larger-diameter portion 27 is arranged in front of the insulated chip 15. As a result, the additional and local injection to the submucosal layer P4 can be easily performed.

Since the operating wire 20 is supported by the smaller-diameter hole portion 16b as the opening hole 16 has the larger-diameter hole portion 16a and the smaller-diameter hole portion 16b, the electrode portion 25 can be kept from rattling (moving more than needed) with respect to the insulated chip 15. Moreover, the larger-diameter hole portion 16a is provided in a portion connected with the guide hole 28 in the opening hole 16, and as seen in the direction of the axis C1 in the pull-back state, the guide hole 28 is configured so as to be arranged inside the outer edge 16c of the larger-diameter hole portion 16a. As a result, the pressure on the distal end side in the direction of the axis C1 can be made to act on the whole cross-section of a proximal end portion of the guide hole 28 by the physiological salt solution within the larger-diameter hole portion 16a, and the physiological salt solution can be effectively poured into the guide hole 18 from the inside of the larger-diameter hole portion 16a. Accordingly, in the pull-back state, the physiological salt solution can be easily injected toward the front of the electrode portion 25 through the opening hole 16 and the guide hole 28.

In the pull-back state, the distal end portion of the sheath 10 covers a portion of the chamfered portion 27c of the larger-diameter portion 27. Therefore, the physiological salt solution can be kept from flowing out in the radial direction from the portions where the respective auxiliary electrodes 29 abut against the insulated chip 15.

Since the larger-diameter portion 27 is formed from a material having insulation, the rod-shaped electrode 26 and the respective auxiliary electrodes 29 can be kept from coming into contact with the non-excised tissue P3 unintentionally to incise the non-excised tissue P3.

By including the auxiliary electrode 29, a tissue can also be incised by moving the electrode portion 25 in the direction of the axis C1 to hook up the tissue with the electrode portion 25.

Since the respective auxiliary electrodes 29 are formed in a rod shape, a broad application range of a high-frequency voltage in the direction in which the auxiliary electrodes 29 extend can be ensured, and the area of the electrodes as seen in the direction of the axis C1 can be reduced.

The respective auxiliary electrodes 29 are arranged at intervals in the circumferential direction, and the respective auxiliary electrodes 29 are configured so as not to overlap the guide hole 28 as seen in the direction of the axis C1. As a result, in the pull-back state, the auxiliary electrodes 29 can be arranged on the proximal end surface 27b of the larger-diameter portion 27 while ensuring a space where the physiological salt solution within the opening hole 16 flows into the guide hole 28.

By bringing the high-frequency knife 1 into the pull-back state and injecting the physiological salt solution, the distance from the observation unit provided at the insertion section of the endoscope to the distal end portion of the guide hole 28 of the electrode portion 25 where the physiological salt solution is injected becomes short. When the electrode portion 25 is made to face the blood P5 that has flowed out, the distance from the observation unit to the blood P7 can be shortened. Therefore, the physiological salt solution can be reliably injected to the blood P7 from the guide hole 28 of the electrode portion 25 while confirming an image acquired in the observation unit by the monitor.

In the present embodiment, the three auxiliary electrodes 29 are radially provided on the proximal end surface 27b of the larger-diameter portion 27. However, the number of auxiliary electrodes 29 provided on the proximal end surface 27b is not limited, and may be one or two, or may be four or more.

Figure 13:
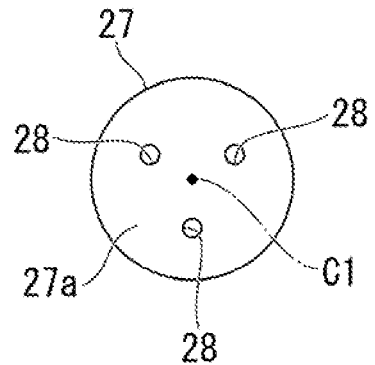
FIG. 13 is a front view of a larger-diameter portion in a high-frequency knife of a modification example of the first embodiment of the present invention.
Figure 14:
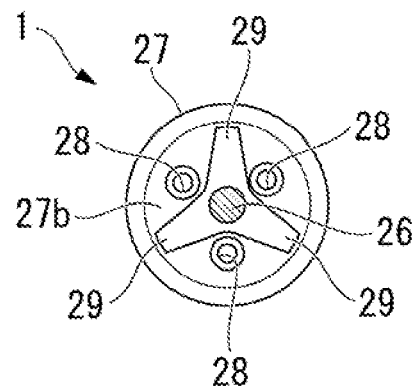
FIG. 14 is a back view of the larger-diameter portion.

Although one guide hole 28 is formed in the larger-diameter portion 27, the number of guide holes 28 formed in the larger-diameter portion 27 may be two or more. In this case, the respective guide holes 28 are formed in the larger-diameter portion 27 so as not to overlap the respective auxiliary electrodes 29 as seen in the direction of the axis C1. Among these, as shown in FIGS. 13 and 14, it is preferable to form three guide holes 28 of the same number as the auxiliary electrodes 29 in the larger-diameter portion 27. In this case, the respective guide holes 28 are formed at equal angles around the axis C1.

In this way, by forming the three guide holes 28 in the larger-diameter portion 27, the balance of arrangement between the auxiliary electrodes 29 and the guide holes 28 can be improved, and incision of a tissue or injection of the physiological salt solution can be more equally performed irrespective of the orientation of the auxiliary electrodes and the guide holes around the axis C1.

In the present embodiment, the auxiliary electrodes 29 formed in the shape of a square bar have been described as an example. However, the shape of the auxiliary electrodes is not limited to this, and may be a shape, such as a semicylinder, in which the cross-section of the auxiliary electrodes 29 in the longitudinal direction is semicircular, as long as the shape that extends in the radial direction of the sheath 10 is provided. In this case, the auxiliary electrodes are formed so as to protrude to the proximal end side, and are arranged on the proximal end surface 27b of the larger-diameter portion 27.

The configuration of the guide hole 28, the auxiliary electrodes 29, or the like of the high-frequency knife 1 of the present embodiment can be variously modified as described below.

Figure 15:
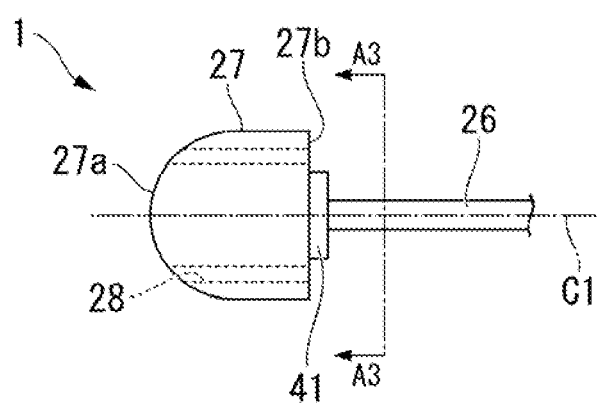
FIG. 15 is a side view of a distal end portion in the high-frequency knife of the modification example of the first embodiment of the present invention.
Figure 16:
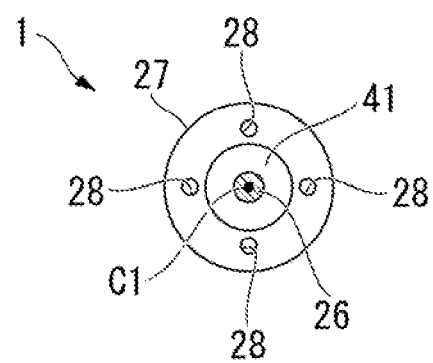
FIG. 16 is a cross-sectional view of cutting line A3-A3 in FIG. 15.

For example, as shown in FIGS. 15 and 16, an auxiliary electrode 41 is formed in the shape of a ring, and guide holes 28 may be formed at the positions of the larger-diameter portion 27 outside the auxiliary electrode 41 as seen in the direction of the axis C1.

The auxiliary electrode 41 is formed so as to have a smaller external diameter than the external diameter of the larger-diameter portion 27, and is arranged on the proximal end surface 27b of the larger-diameter portion 27.

The guide holes 28 are formed so as to extend in the direction of the axis C1. In this modification example, four guide holes 28 are formed in the larger-diameter portion 27. However, as long as the guide holes 28 are formed at the positions outside the auxiliary electrode 41 as seen in the direction of the axis C1, the number of guide holes 28 formed in the larger-diameter portion 27 is not limited to this, and may be one to three or may be five or more.

By configuring the auxiliary electrode 41 in this way, a mucous membrane hooked up near the distal end of the rod-shaped electrode 26 can be reliably incised irrespective of the position of the mucous membrane in the circumferential direction.

Figure 17:
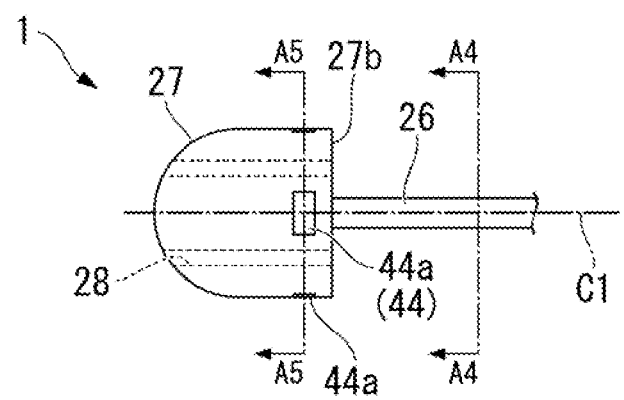
FIG. 17 is a side view of the distal end portion in the high-frequency knife of the modification example of the first embodiment of the present invention.
Figure 18:
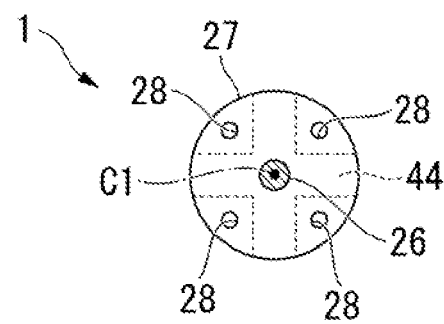
FIG. 18 is a cross-sectional view of cutting line A4-A4 in FIG. 17.
Figure 19:
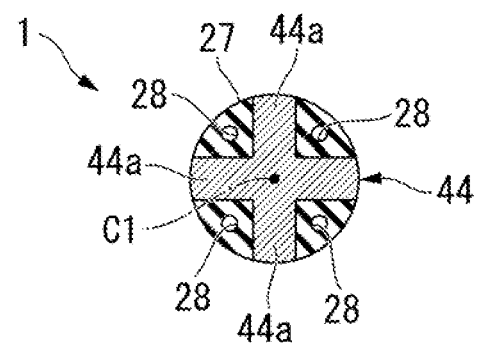
FIG. 19 is a cross-sectional view of cutting line A5-A5 in FIG. 17.

As shown in FIGS. 17 to 19, a portion of the auxiliary electrode 44 may be configured so as to be buried in the larger-diameter portion 27. In this modification example, the auxiliary electrode 44 is formed in the shape of a cross as seen in the direction of the axis C1. Distal ends of four arm portions 44a of the auxiliary electrode 44 formed in the shape of a cross are exposed to the outside from a side surface of the larger-diameter portion 27.

The distal end portion of the rod-shaped electrode 26 extends to the inside of the larger-diameter portion 27, and the rod-shaped electrode 26 and the auxiliary electrode 44 are electrically connected together within the larger-diameter portion 27.

The four guide holes 28 are formed in the larger-diameter portion 27 at positions that do not overlap the auxiliary electrode 44 as seen in the direction of the axis C1.

In the high-frequency knife 1 of this modification example, a mucous membrane cannot be incised by the auxiliary electrode 44 in a state where the mucous membrane is hooked up on the larger-diameter portion 27. However, the auxiliary electrode 44 is used as an electrode that assists the rod-shaped electrode 26 when the larger-diameter portion 27 is moved in the transverse direction and incision is performed by the rod-shaped electrode 26.

Figure 20:
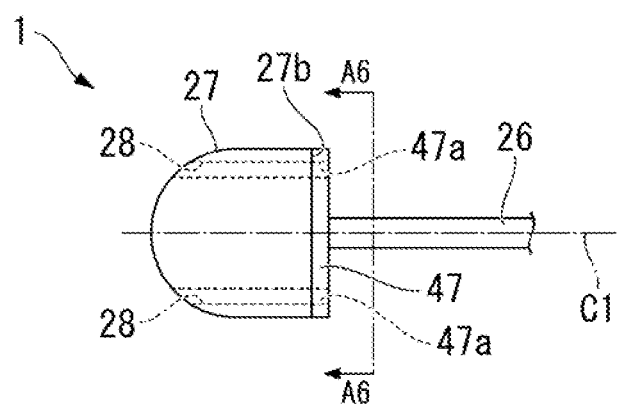
FIG. 20 is a side view of the distal end portion in the high-frequency knife of the modification example of the first embodiment of the present invention.
Figure 21:
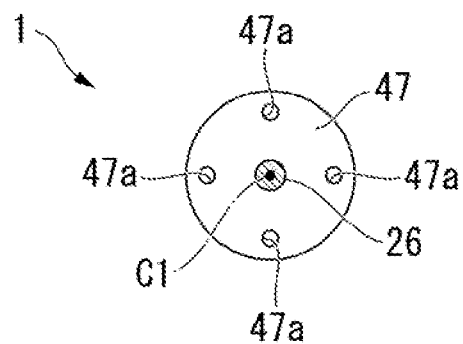
FIG. 21 is a cross-sectional view of cutting line A6-A6 in FIG. 20.

As shown in FIGS. 20 and 21, an auxiliary electrode 47 may be formed over almost the whole surface of the proximal end surface 27b of the larger-diameter portion 27. In this modification example, four through-holes 47a extending in the direction of the axis C1 are formed in the auxiliary electrode 47. The four through-holes 47a are formed at equal angles around the axis C1.

Four guide holes 28 are formed in the larger-diameter portion 27. The guide holes 28 communicate with the through-holes 47a, respectively.

In the high-frequency knife 1 of this modification example, the area of the auxiliary electrode 47 can be made widest on the proximal end surface 27b of the larger-diameter portion 27.

Figure 22:
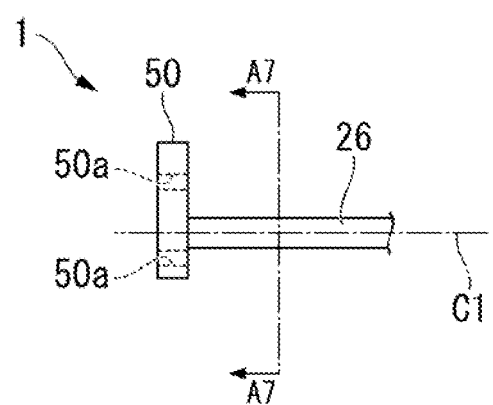
FIG. 22 is a side view of the distal end portion in the high-frequency knife of the modification example of the first embodiment of the present invention.
Figure 23:
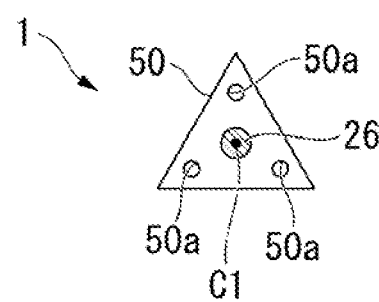
FIG. 23 is a cross-sectional view of cutting line A7-A7 in FIG. 22.

In the modification example shown in FIGS. 22 and 23, a larger-diameter portion 50 is formed in the shape of an equilateral triangular plate as seen in the direction of the axis C1. The larger-diameter portion 50 is formed from metal, such as stainless steel, and the distal end portion of the rod-shaped electrode 26 is electrically connected to a central portion in a proximal end surface of the larger-diameter portion 50. The larger-diameter portion 50 is formed with three guide holes 50a that extend in the direction of the axis C1 and pass through the larger-diameter portion 50. Three guide holes 28 are formed at equal angles around the axis C1.

That is, in this modification example, the larger-diameter portion 50 also serves as the auxiliary electrode.

Figure 24:
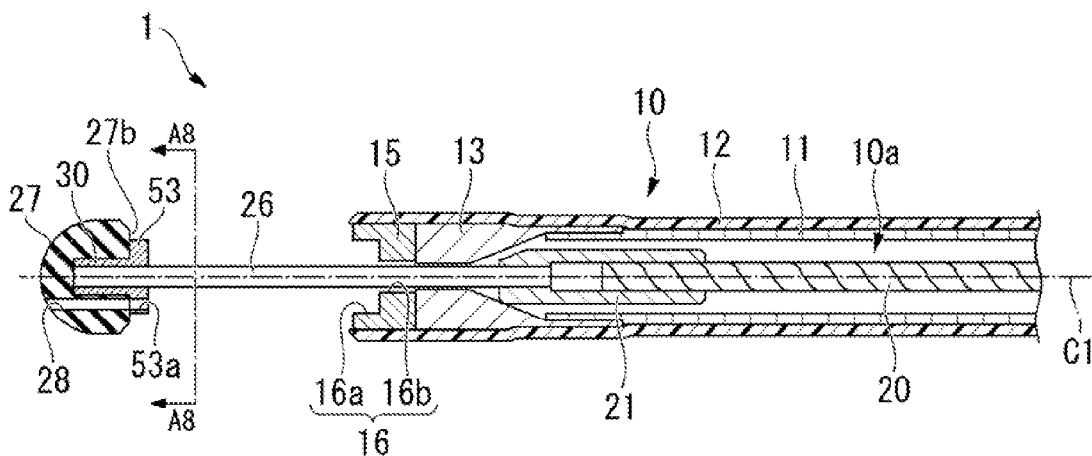
FIG. 24 is a side view of the distal end portion when the high-frequency knife of the modification example of the first embodiment of the present invention is brought into the push-in state.
Figure 25:
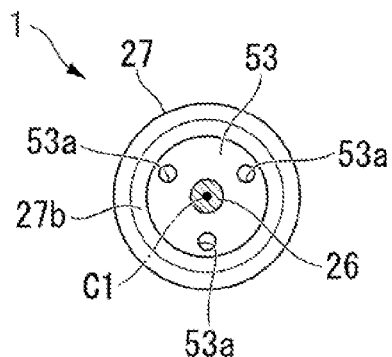
FIG. 25 is a cross-sectional view of cutting line A8-A8 in FIG. 24.

Additionally, in a modification example shown in FIGS. 24 and 25, the external diameter of a ring-shaped auxiliary electrode 53 formed on the proximal end surface 27b of the larger-diameter portion 27 is set so as to be slightly smaller than the internal diameter of the larger-diameter hole portion 16a of the opening hole 16. The thickness (the length in the direction of the axis C1) of the auxiliary electrode 53 is set to be smaller than the length of the larger-diameter hole portion 16a in the direction of the axis C1. Three through-holes 53a extending in the direction of the axis C1 are formed in the auxiliary electrode 53. The three through-holes 53a are formed at equal angles around the axis C1.

Three guide holes 28 are formed in the larger-diameter portion 27. The guide holes 28 communicate with the through-holes 53a, respectively.

Figure 26:
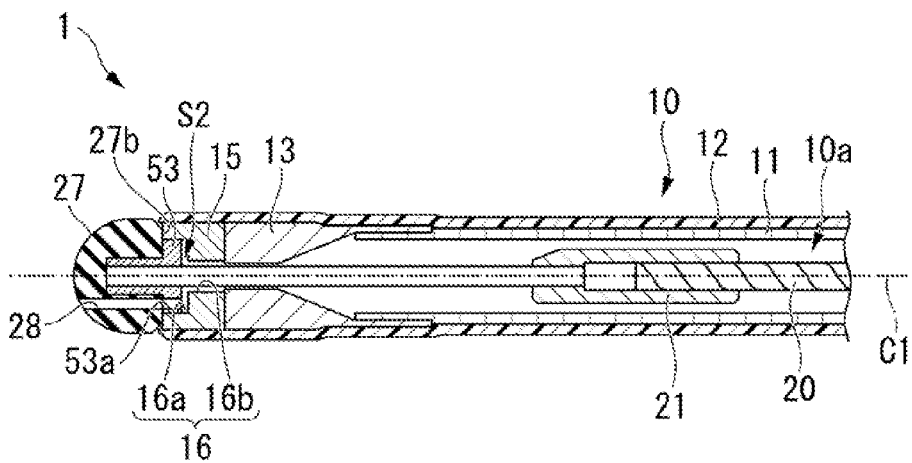
FIG. 26 is a cross-sectional view of a side surface of the distal end portion when the high-frequency knife is brought into the pull-back state.

When the high-frequency knife 1 of the present modification example configured in this way is brought into the pull-back state, as shown in FIG. 26, the auxiliary electrode 53 enters the larger-diameter hole portion 16a, and the proximal end surface 27b of the larger-diameter portion 27 abuts against the insulated chip 15. At this time, since the thickness of the auxiliary electrode 53 is set to be smaller than the length of the larger-diameter hole portion 16a in the direction of the axis C1, spacing S2 is formed between the end surface (bottom surface) of the larger-diameter hole portion 16a on the side of the smaller-diameter hole portion 16b, and the auxiliary electrode 53.

In this modification example, in the pull-back state, the spacing S2 is formed between the bottom surface of the larger-diameter hole portion 16a and the auxiliary electrode 53. Therefore, the physiological salt solution supplied from the syringe D is injected to the front of the larger-diameter portion 27 through the conduit line 10a, the smaller-diameter hole portion 16b, the spacing S2, the through-holes 53a of the auxiliary electrode 53, and the guide holes 28.

Additionally, since the auxiliary electrode 53 enters the larger-diameter hole portion 16a, the larger-diameter portion 27 can be kept from rattling with respect to the insulated chip 15, or the physiological salt solution can be kept from flowing out from between the insulated chip 15 and the larger-diameter portions 27.

Second Embodiment

Next, although a second embodiment of the present invention will be described referring to FIGS. 27 to 30, the same parts as the above embodiment will be designated by the same reference numerals and the description thereof will be omitted, and only different points will be described.

Figure 27:
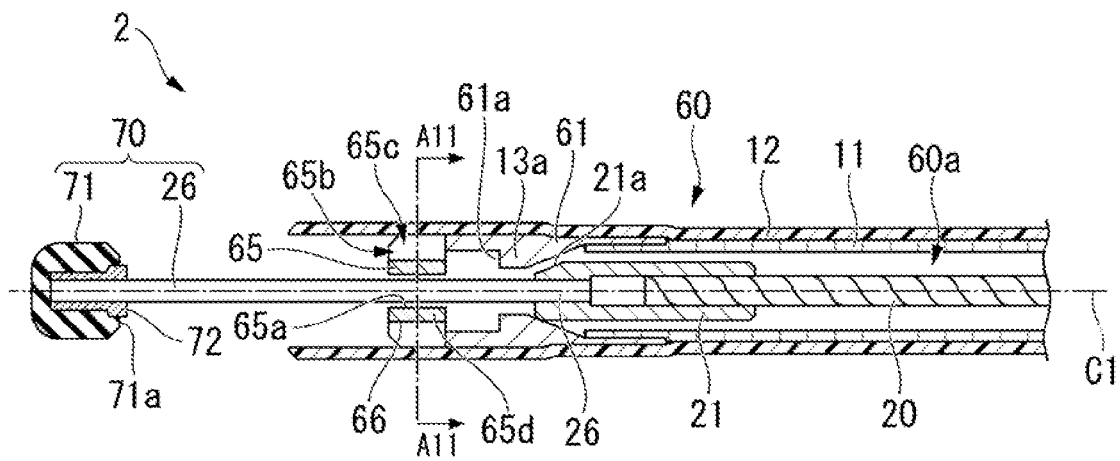
FIG. 27 is a cross-sectional view of a side surface of a distal end portion when a high-frequency knife of the second embodiment of the present invention is brought into the push-in state.
Figure 28:
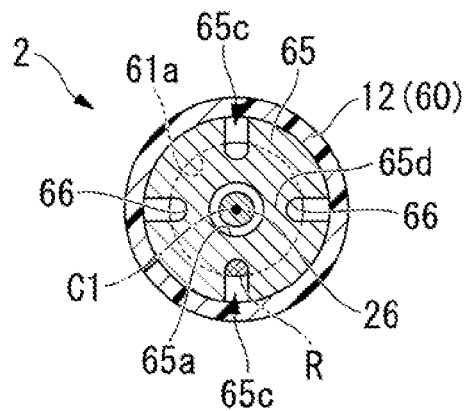
FIG. 28 is a cross-sectional view of cutting line A11-A11 in FIG. 27.

As shown in FIGS. 27 and 28, a high-frequency knife 2 of the present embodiment includes a sheath 60, an insulated chip 65, and a larger-diameter portion 71 instead of the sheath 10, the insulated chip 15, and the larger-diameter portion 27 of the high-frequency knife 1 of the first embodiment.

The sheath 60 includes a stopper member 61 instead of the stopper member 13 of the first embodiment of the sheath 10. In addition to the configuration of the stopper member 13 of the first embodiment, the stopper member 61 is formed with a step portion 61a recessed from the distal end surface of the thick portion 13a to the proximal end side. The step portion 61a is formed over the whole circumference around the axis C1.

The insulated chip 65 is formed in a substantially columnar shape from the same material as the insulated chip 15. The insulated chip 65 is formed with a second opening hole 65a passing through the insulated chip 65 in the direction of the axis C1 on an axis C1. The second opening hole 65a communicates with a conduit line 60a of the sheath 60.

The edge of the insulated chip 65 is formed with a slit (opening hole) 66 communicating with a distal end-side opening (opening) 65b formed in a distal end surface, a side-surface-side opening 65c formed in a side surface, and the conduit line 60a, respectively. The side-surface-side opening 65c is formed over the total length of the insulated chip 65 in the direction of the axis C1. The distal end-side opening 65b and the side-surface-side opening 65c communicate with each other. A slit 66 is formed in the shape of a groove that passes through the insulated chip 65 in the direction of the axis C1 and communicates with the side-surface-side opening 65c, as a whole.

In this example, four slits 66 are formed at equal angles around the axis C1 in the insulated chip 65.

As seen in the direction of the axis C1 shown in FIG. 28, the respective slits 66 and the second opening hole 65a are provided so as to be shifted from each other (so as not to overlap each other). That is, the insulated chip 65 is formed with a wall portion 65d for separating the slits 66 and the second opening hole 65a. Moreover, a space within the step portion 61a that is a distal end portion of the conduit line 60a and the slits 66 are formed so as to overlap each other at least partially. In this example, the space in the step portion 61a and the slits 66 overlap each other in regions R to form passages.

As shown in FIGS. 27 and 28, the rod-shaped electrode 26 is inserted through the second opening hole 65a. The distal end of the sheath 60 is formed so as to extend further toward the distal end side than the insulated chip 65.

In the present embodiment, the larger-diameter portion 71 is formed in the shape of a column with round corners. The larger-diameter portion 71 is formed so as to have an external diameter that is smaller than the external diameter of the insulated chip 65 and the internal diameter of the insulating tube 12 and larger than the external diameter of the rod-shaped electrode 26. The larger-diameter portion 71 can be formed from the same material as that of the larger-diameter portion 27 having electrical insulation.

A ring-shaped auxiliary electrode 72 is provided on a proximal end surface 71a of the larger-diameter portion 71 in a state where the auxiliary electrode is exposed to the proximal end side.

The rod-shaped electrode 26 and the larger-diameter portion 71 constitute an electrode portion 70.

If the high-frequency knife 2 configured in this way, as shown in FIG. 27, pushes the operating wire 20 into the distal end side with respect to the sheath 60, the stopper-receiving portion 21 abuts against the stopper member 61, and there is positioning the push-in state where the operating wire 20 is pushed into the distal end side.

Figure 29:
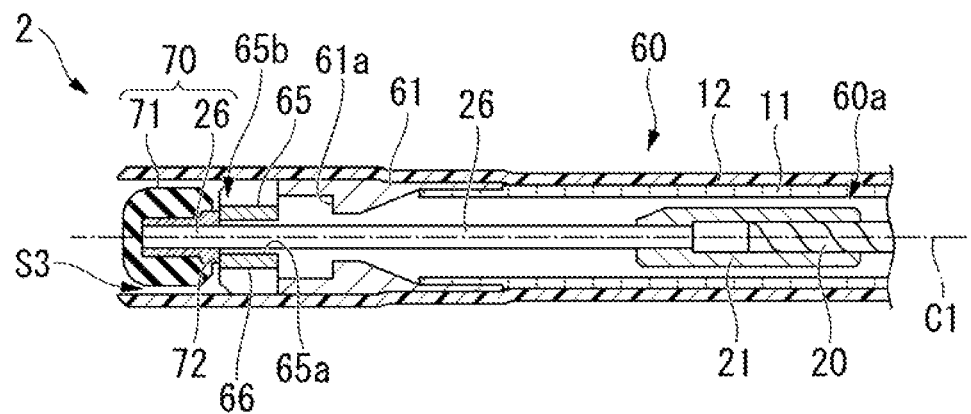
FIG. 29 is a cross-sectional view of the side surface of the distal end portion when the high-frequency knife is brought into the pull-back state.
Figure 30:
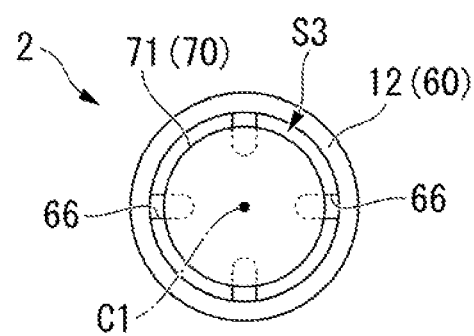
FIG. 30 is a front view when the high-frequency knife is brought into the pull-back state.

On the other hand, if the operating wire 20 is pulled back to the proximal end side with respect to the sheath 60, as shown in FIGS. 29 and 30, there is positioning in the pull-back state where the operating wire 20 is pulled back to the proximal end side as the larger-diameter portion 71 abuts against the insulated chip 65 via the auxiliary electrode 72. At this time, the auxiliary electrode 72 provided on the larger-diameter portion 71 is configured so as to block the second opening hole 65a. Spacing S3 is formed between the insulating tube 12 and the larger-diameter portion 71. A portion of the distal end-side opening 65b is brought into the non-blocked state by the larger-diameter portion 71 due to the spacing S3.

Next, only different points from the high-frequency knife 1 of the above embodiment will be described regarding the operation of the high-frequency knife 2 configured as described above.

Since the process of bringing the high-frequency knife 2 into the push-in state to incise a tissue is the same as that of the embodiment, the description thereof is omitted.

If the physiological salt solution is supplied to the conduit line 60a of the sheath 60 by the syringe D by bringing the high-frequency knife 2 into the pull-back state, the supplied physiological salt solution is injected toward the front of the insulating tube 12 and the larger-diameter portion 71 through the space within the step portion 61a of the stopper member 61, the respective slits 66, and the spacing S3. Since the space within the step portion 61a and the slits 66 overlap each other in the regions R, the physiological salt solution disposed in the regions R as seen in the direction of the axis C1 in the space within the step portion 61a is delivered forward without striking the insulated chip 65 if the pressure on the distal end side in the direction of the axis C1 is applied.

As described above, according to the high-frequency knife 2 of the present embodiment, in the pull-back state, the larger-diameter portion 71 does not become an obstacle to the injection of the physiological salt solution.

The physiological salt solution can be easily injected toward the front through the slits 66 by forming the slits 66 in the insulated chip 65 separately from the second opening hole 65a through which the rod-shaped electrode 26 is inserted.

Since the slits 66 are formed in the side-surface-side opening 65c communicating with the distal end-side opening 65b, the physiological salt solution sent into the slits 66 can be made to flow to a radial outer side within the insulating tube 12 through the side-surface-side opening 65c and can be made to flow toward the front in a place on this radial outer side. Since the larger-diameter portion 71 does not easily become an obstacle when the physiological salt solution flows toward the front in the place on the radial outer side within the insulating tube 12, the pressure loss when the physiological salt solution is made to flow within the insulating tube 12 can be reduced.

The larger-diameter portion 71 is formed to have a smaller external diameter than the external diameter of the insulated chip 65. For this reason, the spacing S3 is formed between the insulating tube 12 supported by the insulated chip 65 and the larger-diameter portion 71, and the physiological salt solution passed through the spacing S3 can be guided by the insulating tube 12 and the larger-diameter portion 71 so as to be directed to the front.

As seen in the direction of the axis C1, the space within the step portion 61a and the slits 66 overlap each other in the regions R. For this reason, the pressure loss when the physiological salt solution disposed in the regions R as seen in the direction of the axis C1 within the space in the step portion 61a is delivered to the distal end side in the direction of the axis C1 can be reduced, and the amount of the physiological salt solution injected toward the front can be increased.

When the high-frequency knife 2 is brought into the pull-back state, the auxiliary electrode 72 blocks the second opening hole 65a. Therefore, the physiological salt solution can be prevented from flowing toward the front through the second opening hole 65a, and the physiological salt solution supplied from the syringe D can be guided so as to pass through the slits 66.

Since the larger-diameter portion 71 is formed from a material having insulation, the rod-shaped electrode 26 and the respective auxiliary electrodes 72 can be kept from coming into contact with the non-excised tissue unintentionally to incise the non-excised tissue.

In the present embodiment, for example, in a case where the physiological salt solution is apt to flow toward the front within the sheath 60 as in a case where the spacing S3 is relatively large, the side-surface-side opening 65c may be formed only on the distal end side in the direction of the axis C1. Moreover, the slits 66 may be configured so as not to include the side-surface-side opening 65c, that is, may be communication holes that pass through the insulated chip 65 in the direction of the axis C1.

The distal end of the sheath 60 may be configured so as to be located further toward the proximal end side than the distal end portion of the insulated chip 65. This is because, even if the distal end of the sheath is configured in this way, the physiological salt solution passing through the space within the step portion 61a and through the slits 66 can be injected toward the front.

In the present embodiment, the four slits 66 are formed in the insulated chip 65. However, the number of slits 66 formed in the insulated chip 65 is not limited to this, and may be one to three or may be or five or more.

Although the preferred examples of the present invention have been described above, the present invention is not limited to these examples. Additions, omissions, substitutions, and other modifications of the configuration can be made without departing from the concept of the present invention. The present invention is not to be considered as being limited by the foregoing description, and is limited only by the scope of the appended claims. Moreover, it is obvious that the respective configurations shown in the respective embodiments may be combined and used appropriately.

For example, in the first embodiment and the second embodiment, the auxiliary electrode may not be included when the electrode portion is not moved in the longitudinal direction for use.

Additionally, although the physiological salt solution is used as the fluid, a medical fluid or the like can be appropriately selected and used in addition to this physiological salt solution.

The invention claimed is:

1. A high-frequency knife comprising:
a sheath having a flexibility and in which a conduit line that is communicated with a fluid source supplying a fluid is formed;
a supporting member which is provided on an inner peripheral surface of a distal end portion of the sheath and has electric insulation; and
an electrode portion which has a rod-shaped electrode that is capable of advancing and retracting with respect to the supporting member, and a larger-diameter portion provided at a distal end of the rod-shaped electrode, an outer diameter of the larger-diameter portion being larger than that of the rod-shaped electrode,
wherein the supporting member is formed with an opening hole which passes through the supporting member in an axial direction of the sheath, into which the rod-shaped electrode is inserted, and which communicates with the conduit line of the sheath,
wherein a guide hole is formed in the larger-diameter portion so as to pass through from a proximal end of the larger-diameter portion to a distal end thereof,
wherein the guide hole is located further toward a radial inner side than an outer edge of the opening of a distal end of the opening hole and further toward a radial outer side than the rod-shaped electrode and overlaps the opening of the distal end of the opening hole in the direction of a longitudinal axis of the rod-shaped electrode,
wherein a distal end of the sheath extends further toward the distal end side than the supporting member,
wherein the fluid that is supplied through the conduit from the fluid source is capable of flowing through a gap between an outer peripheral surface of the rod-shaped electrode and an inner peripheral surface of the opening hole,
wherein the fluid is injected to a front of the larger-diameter portion through the guide hole by covering an edge of a proximal end surface of the larger-diameter portion with the radial outer side of the distal end portion and communicating with the opening hole and the guide hole in a pull-back state where the electrode portion is pulled back toward a proximal end portion of the sheath.

2. The high-frequency knife according to claim 1,
wherein the opening hole includes:
a larger-diameter hole portion which is formed on a distal end side of the supporting member; and
a smaller-diameter hole portion which is formed on a proximal end side of the larger-diameter hole portion, an internal diameter of the smaller-diameter hole portion is smaller than that of the larger-diameter hole portion,
wherein the internal diameter of the larger-diameter hole portion is smaller than an external diameter of the larger-diameter portion, and
wherein the larger-diameter portion and an edge of the larger-diameter hole portion abut each other in the pull-back state.

3. The high-frequency knife according to claim 2,
wherein the larger-diameter portion has electric insulation.

4. The high-frequency knife according to claim 3,
wherein the electrode portion includes an auxiliary electrode, which is formed on a proximal end side of the larger-diameter portion so as to extend further in a radial direction than the rod-shaped electrode.

5. The high-frequency knife according to claim 4,
wherein the internal diameter of the larger-diameter hole portion is larger than the radial dimension of the auxiliary electrode, and
wherein at least a portion of the auxiliary electrode enters the larger-diameter hole portion in the pull-back state.

6. The high-frequency knife according to claim 5,
wherein the guide hole communicates with a through-hole formed in the auxiliary electrode so as to extend in the axial direction of the sheath.

* * * * *